US00PP15590P2

(12) United States Plant Patent
Talmadge

(10) Patent No.: US PP15,590 P2
(45) Date of Patent: Feb. 22, 2005

(54) ***NEMESIA* PLANT NAMED 'BALARTUBLUE'**

(50) Latin Name: *Nemesia foetans*
Varietal Denomination: Balartublue

(75) Inventor: Paul A. Talmadge, Guadalupe, CA (US)

(73) Assignee: Ball Horticultural Company, West Chicago, IL (US)

( * ) Notice: Subject to any disclaimer, the term of this patent is extended or adjusted under 35 U.S.C. 154(b) by 14 days.

(21) Appl. No.: 10/734,859

(22) Filed: Dec. 12, 2003

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—Wood, Phillips, Katz, Clark & Mortimer

(57) ABSTRACT

A new and distinct cultivar of *Nemesia* plant named 'Balartublue', characterized by its violet-blue-colored flowers, medium green-colored foliage, and upright, spreading growth habit.

1 Drawing Sheet

Latin name of genus and species of plant claimed: *Nemesia foetans.*
Variety denomination: 'Balartublue'.

BACKGROUND OF THE INVENTION

The present invention relates to a new and distinct cultivar of *Nemesia* plant botanically known as *Nemesia foetans* and hereinafter referred to by the cultivar name 'Balartublue'.

The new cultivar was developed by the inventor in a controlled breeding program during the fall of 2000, at Guadalupe, Calif. The objective of the breeding program was the development of *Nemesia* cultivars with a well-branched, spreading growth habit, unique flower colors and continuous flowering.

The female parent of 'Balartublue' was the proprietary *Nemesia foetans* selection designated '10056' (not patented) characterized by its slate blue-colored flowers, medium green-colored foliage, and upright habit. The male parent of 'Balartublue' was the proprietary *Nemesia foetans* selection designated '10050' (not patented) characterized by its indigo blue-colored flowers, dark green-colored foliage, and upright growth habit. The new cultivar was discovered and selected by the inventor as a single flowering plant from within the progeny of the above stated cross-pollination during the winter of 2000 in a controlled environment at Guadalupe, Calif. and was initially designated '2031-6'.

Asexual reproduction of the new cultivar by terminal stem cuttings since the winter of 2000 at Guadalupe, Calif. and West Chicago, Ill. has demonstrated that the new cultivar reproduces true to type with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

It was repeatedly found that the cultivar of the present invention:

1. Exhibits violet-blue colored flowers.
2. Forms medium green-colored foliage, and
3. Exhibits an upright and spreading growth habit.

Plants of the new cultivar differ from plants of the female parent primarily in floriferousness and growth habit, and from plants of the male parent primarily in floriferousness and foliage color.

Of the many *Nemesia* cultivars known to the inventor, the most similar to 'Balartublue' is the *Nemesia* cultivar 'Hubbird' (U.S. Plant Pat. No. 12,014). However, in side by side comparisons, plants of the new cultivar differ from plants of 'Hubbird' in the following characteristics:

1. Plants of the new cultivar are less floriferous than plants of 'Hubbird', and
2. Plants of the new cultivar exhibit a more compact growth habit than plants of 'Hubbird'.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs differ slightly from color values cited in the detailed description which accurately describe the colors of 'Balartublue'. The plants were grown in 10 cm pots for 10 weeks in a greenhouse at West Chicago, Ill.

DETAILED BOTANICAL DESCRIPTION

Figure 1:
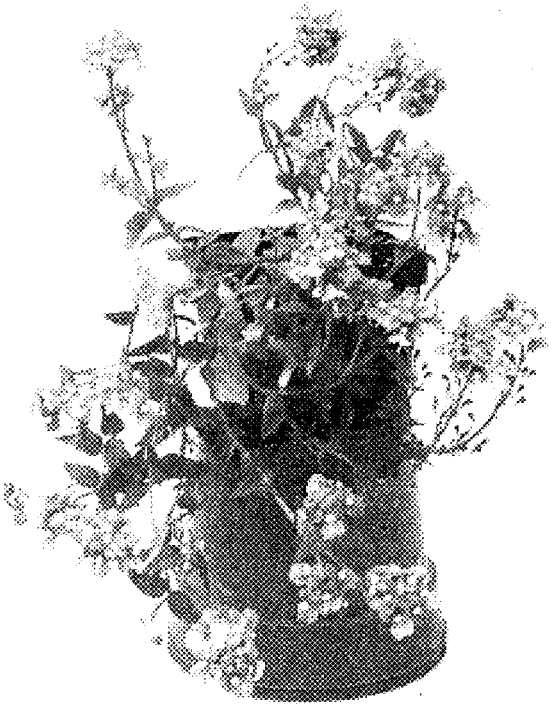
FIG. 1 illustrates a side view of the overall growth and flowering habit of 'Balartublue'.
Figure 2:
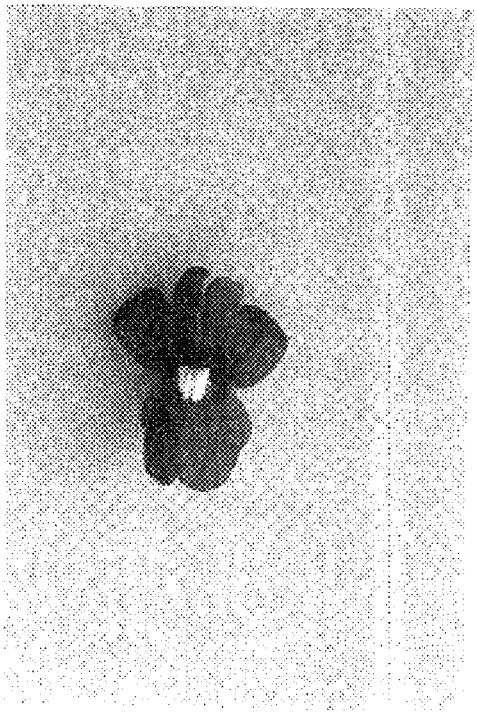
FIG. 2 illustrates a close-up view of an individual flower of 'Balartublue'.

The chart used in the identification of colors described herein is The R.H.S. Colour Chart of The Royal Horticultural Society, London, England 1995 edition, except where color terms of ordinary significance are used. The color values were determined on May 14, 2003. The readings were taken between 1:00 and 3:00 p.m. under natural daylight conditions. The plants were produced from cuttings taken from stock plants and were grown in a double polycarbonate-covered greenhouse under conditions comparable to those used in commercial practice. The plants were grown in 10 cm pots for 10 weeks while utilizing a soilless growth medium. Greenhouse temperatures were maintained at approximately 65°–75° F. (18°–24° C.) during the day and approximately 50°–60° F. (10°–15° C.) during the night. Greenhouse light levels were maintained at approximately 4,000 to 7,000 footcandles during the day.

Botanical classification: *Nemesia foetans,* cultivar 'Balartublue'.

Parentage:

*Female parent.*—Proprietary *Nemesia foetans* selection designated '10056' (not patented).

*Male parent.*—Proprietary *Nemesia foetans* selection designated '10050' (not patented).

Propagation:

*Type cutting.*—Terminal stem.

*Time to initiate roots.*—Approximately 7 to 10 days.

*Time to develop roots.*—Approximately 21 to 28 days.

*Root description.*—Fine and fibrous.

*Rooting habit.*—Freely branching.

Plant description:

*Habit of growth.*—Moderately vigorous with good branching. An average of 3 primary branches and 20 secondary lateral branches develop after pinching.

*Form.*—Upright and outwardly spreading.

*Size.*—A mature plant, 10 weeks after the planting of a rooted cutting, commonly measures approximately 16.4 cm in height from soil level to top of foliage and approximately 37.1 cm in diameter (area of spread).

*Primary branch.*—Shape: Tetragonal. Appearance: Wiry. Strength: Moderate. Length: Approximately 30.3 cm. Diameter: Approximately 3 mm. Texture: Glabrous. Internode length at middle of branch: Approximately 3.9 cm. Color: Darker than 144A.

*Secondary lateral branches.*—Shape: Tetragonal. Length: Approximately 18.1 cm. Diameter: approximately 1.8 mm. Color: 144A.

*Foliage.*—Type: Single. Fragrance: None. Arrangement: Opposite. Quantity per branch: Approximately 8. Orientation to stem: Acute. Shape: Ovate. Margin: Serrate. Apex: Acute. Base: Decurrent. Length of leaf taken from middle of branch: Approximately 3.3 cm. Leaf width: Approximately 1.7 cm. Texture of upper and lower surfaces: Glabrous. Venation pattern: Pinnate. Color of upper and lower surfaces of young foliage: 144A. Color of mature foliage: Upper surface: Darker than 137A with venation of 144B. Lower surface: 137C with venation of 144B.

Flowering description:

*Flowering habit.*—Freely flowering.

*Natural flowering season.*—Year round in greenhouse environment and spring through autumn in outdoor garden.

*Inflorescence type/description.*—Terminal racemes. Length: 4 cm. Width: 3.6 cm. Number per plant: Approximately 13.4 fully open racemes and 8.8 developing racemes per plant. Number of fully open flowers per raceme at any one time: 7.

Flower description:

*Type.*—Solitary, zygomorphic, and bilabiate with nectar spur. Flowering is acropetally toward apex. Flowers are persistent and not fragrant.

*Flower size/aspect.*—Length: Approximately 1.8 cm. Width: Approximately 1.5 cm. Depth, including nectar spur: Approximately 1 cm. Aspect: Facing outward and upward.

*Petals.*—Quantity: Five per flower.

*Upper four petals.*—Fused at base forming a lip having two central linear lobes and one outer obovate lobe on each side. Lip width: 1.5 cm. Apex of all lobes: Obtuse. Margin of all lobes: Entire. Length of central lobes: Approximately 9 mm. Width of central lobes: Approximately 4 mm. Length of outer lobes: Approximately 7 mm. Width of outer lobes: Approximately 5 mm.

*Lower petal.*—Has two obovate lobes and is modified into a nectar spur. Petal width: Approximately 1.1 cm. Petal length from palate: Approximately 7 mm. Petal apex: Emarginate. Petal margin: Entire. Spur length: 6 mm. Spur diameter at base: 2 mm. Spur diameter at tip: 0.8 mm. Spur texture: Puberulent. Spur color: 150D with streaks of N87B.

*Petal color.*—When first open: Upper surface of all lobes: 86A. Lower surface of all lobes: 93C. Mature lobes: Upper surface: Between 90B and 90C with palate of 2C. Lower surface: 85D. Upper surface fades with age to: 90D. Lower surface fades with age to: 85D. Palate color fades with age to: 2D.

*Peduncle.*—Shape: Tetragonal. Strength: Strong. Surface texture: Densely pubescent. Angle to the stem: Acute. Length: Approximately 3.8 cm. Diameter: Approximately 1 mm. Color: 144A.

*Pedicel.*—Length: Approximately 1.3 cm. Diameter: Approximately 1 mm. Angle to stem: Acute. Strength: Strong. Texture: Dense short, soft, glandular pubescence. Color: Darker than 144A.

*Bud.*—Shape: Ovoid with spur. Length: Approximately 4.5 mm. Diameter: Approximately 4.8 mm. Color: 145C.

*Calyx.*—Shape: Star. Width: Approximately 6 mm. Formed by five sepals fused at base. Sepal shape: Lanceolate. Sepal margin: Entire. Sepal apex: Acute. Sepal length: Approximately 4 mm. Sepal width: Approximately 2 mm. Sepal texture: Upper surface is glabrous. Lower surface is densely pubescent. Sepal color: Both surfaces: 137A.

*Reproductive organs.*—Androecium: There are 4 stamens per flower — 2 are 3 mm in length, 2 are 2 mm in length. Filament shape: Curved. Anther shape: Oval. Anther length: 3 mm. Anther color: 166B. Amount of pollen: Abundant. Pollen color: 7A. Gynoecium: Number: One pistil per flower. Pistil length: 2 mm. Stigma length: 0.4 mm. Stigma color: 145C. Style length: 0.7 mm. Style color: 145D. Ovary diameter: 1 mm. Ovary color: N144D.

Seed and fruit production: Neither seed nor fruit production has been observed.

Disease and pest resistance: Resistance to pathogens and pests common to *Nemesia* has not been observed.

Hardiness zone: 'Balartublue' is hardy in zones nine (9) and above.

What is claimed is:

1. A new and distinct cultivar of *Nemesia* plant named 'Balartublue' substantially, as herein shown and described, which:

1. Exhibits violet-blue-colored flowers,
2. Forms medium green-colored foliage, and
3. Exhibits an upright and spreading growth habit.

* * * * *